(12) United States Patent
Bertholds et al.

(10) Patent No.: US 9,816,885 B2
(45) Date of Patent: Nov. 14, 2017

(54) OPTICAL FORCE SENSING ELEMENT AND MICROSURGICAL INSTRUMENT

(75) Inventors: Axel Bertholds, Verscio (CH); Pere Llosas, Minusio (CH); Simon Henein, Neuchatel (CH)

(73) Assignee: SENSOPTIC, SA, Losone (CH)

( * ) Notice: Subject to any disclaimer, the term of this patent is extended or adjusted under 35 U.S.C. 154(b) by 1396 days.

(21) Appl. No.: 13/551,910

(22) Filed: Jul. 18, 2012

(65) Prior Publication Data
US 2013/0204142 A1 Aug. 8, 2013

(30) Foreign Application Priority Data

Feb. 7, 2012 (CH) ..................................... 0164/12

(51) Int. Cl.
| | |
|---|---|
| A61B 6/00 | (2006.01) |
| G01L 5/16 | (2006.01) |
| B23P 11/00 | (2006.01) |
| A61B 17/00 | (2006.01) |
| A61B 90/00 | (2016.01) |

(52) U.S. Cl.
CPC .............. *G01L 5/166* (2013.01); *A61B 90/06* (2016.02); *A61B 2017/00057* (2013.01); *A61B 2017/00526* (2013.01); *A61B 2090/064* (2016.02); *Y10T 29/49826* (2015.01)

(58) Field of Classification Search
None
See application file for complete search history.

(56) References Cited

U.S. PATENT DOCUMENTS

| 5,807,265 | A | * | 9/1998 | Itoigawa et al. ............... 600/486 |
|---|---|---|---|---|
| 6,113,590 | A | * | 9/2000 | Fischer et al. .................. 606/28 |
| 6,120,476 | A | * | 9/2000 | Fung et al. ................. 604/95.04 |
| 6,134,003 | A | * | 10/2000 | Tearney et al. ............... 356/479 |
| 6,173,091 | B1 | * | 1/2001 | Reich ................................ 385/12 |
| 6,272,371 | B1 | * | 8/2001 | Shlomo ......................... 600/424 |
| 6,310,990 | B1 | * | 10/2001 | Putnam et al. ................. 385/12 |

(Continued)

FOREIGN PATENT DOCUMENTS

| WO | WO 2009114955 | 9/2009 |
|---|---|---|
| WO | WO 2012/012565 | 1/2012 |

OTHER PUBLICATIONS

International Search Report, dated May 2, 2012.

*Primary Examiner* — Long V Le
*Assistant Examiner* — Don N Ho
(74) *Attorney, Agent, or Firm* — Dority & Manning, P.A.

(57) ABSTRACT

An optical force sensing element for microsurgical instruments and methods measures force F in three orthogonal directions and includes a monolithic cylinder structure, a cylindrical surface and a top surface that absorbs and transmits the force F. Three punch-like notches, all being parallel to the y-direction, are spaced apart along the z-axis and form two blades between the first and second notch and between the second and the third notch. Three channels parallel to the z-axis extend from the bottom surface to the top surface and cross the first notch while bypassing the other two notches. Three optical fibers, each fixed in one of the three channels, all entering the structure from the bottom surface, cross the first notch and end at or near the top surface while being interrupted in the first notch and forming two surfaces of each fiber that define a Fabry-Perot interferometric cavity.

17 Claims, 3 Drawing Sheets

(56) References Cited

U.S. PATENT DOCUMENTS

| | | | |
|---|---|---|---|
| 6,324,918 B1* | 12/2001 | Gitis et al. | 73/862 |
| 6,563,970 B1* | 5/2003 | Bohnert et al. | 385/13 |
| 6,915,048 B2* | 7/2005 | Kersey et al. | 385/50 |
| 7,050,662 B2* | 5/2006 | Behrmann et al. | 385/13 |
| 7,173,713 B2* | 2/2007 | Xu et al. | 356/480 |
| 7,466,879 B2* | 12/2008 | Tjin | 385/13 |
| 7,491,957 B2* | 2/2009 | Kitamura et al. | 250/559.32 |
| 8,048,063 B2* | 11/2011 | Aeby et al. | 606/1 |
| 8,050,523 B2* | 11/2011 | Younge et al. | 385/13 |
| 8,074,501 B2* | 12/2011 | Kummer et al. | 73/114.19 |
| 8,075,498 B2* | 12/2011 | Leo et al. | 600/587 |
| 8,435,232 B2* | 5/2013 | Aeby et al. | 606/1 |
| 8,567,265 B2* | 10/2013 | Aeby et al. | 73/862.624 |
| 8,659,762 B2* | 2/2014 | Bertholds et al. | 356/498 |
| 8,705,903 B2* | 4/2014 | Younge et al. | 385/13 |
| 8,932,288 B2* | 1/2015 | Leo et al. | 606/41 |
| 8,961,436 B2* | 2/2015 | Leo et al. | 600/587 |
| 2006/0133715 A1* | 6/2006 | Belleville et al. | 385/13 |
| 2006/0200049 A1* | 9/2006 | Leo et al. | 600/587 |
| 2007/0041019 A1* | 2/2007 | Schmidt | 356/480 |
| 2007/0060847 A1* | 3/2007 | Leo et al. | 600/587 |
| 2007/0265503 A1* | 11/2007 | Schlesinger et al. | 600/182 |
| 2008/0009750 A1* | 1/2008 | Aeby et al. | 600/478 |
| 2008/0294144 A1* | 11/2008 | Leo et al. | 604/508 |
| 2009/0177095 A1* | 7/2009 | Aeby et al. | 600/478 |
| 2009/0226128 A1* | 9/2009 | Donlagic et al. | 385/13 |
| 2009/0287092 A1* | 11/2009 | Leo et al. | 600/474 |
| 2009/0306650 A1* | 12/2009 | Govari et al. | 606/41 |
| 2010/0063478 A1* | 3/2010 | Selkee | 604/524 |
| 2010/0064785 A1* | 3/2010 | Kummer et al. | 73/114.19 |
| 2010/0094163 A1* | 4/2010 | Deladi et al. | 600/561 |
| 2010/0328675 A1* | 12/2010 | Bertholds et al. | 356/498 |
| 2011/0087112 A1* | 4/2011 | Leo et al. | 600/478 |
| 2012/0078138 A1* | 3/2012 | Leo et al. | 600/587 |
| 2012/0179068 A1* | 7/2012 | Leo et al. | 600/587 |
| 2012/0265102 A1* | 10/2012 | Leo | A61B 5/6852 600/587 |
| 2014/0121537 A1* | 5/2014 | Aeby et al. | 600/478 |
| 2015/0216612 A1* | 8/2015 | Leo et al. | 600/587 |

* cited by examiner

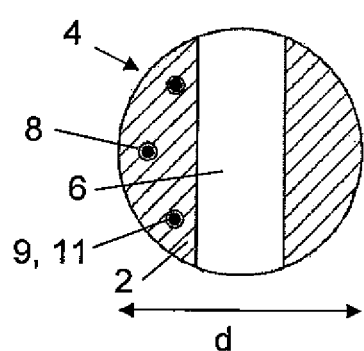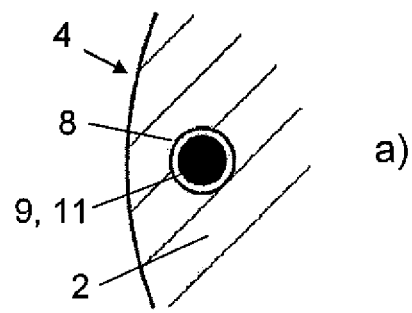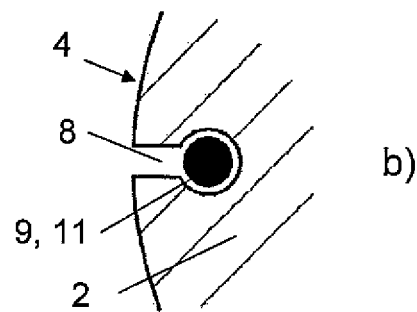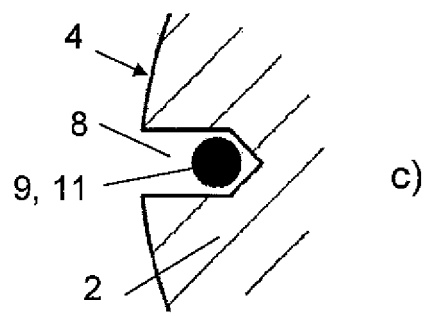
Fig. 5
a)
b)
c)
Fig. 6

OPTICAL FORCE SENSING ELEMENT AND MICROSURGICAL INSTRUMENT

CROSS-REFERENCE TO RELATED APPLICATIONS

This application claims priority to Swiss Application Serial No. 00164/12 filed Feb. 7, 2012.

FIELD OF THE INVENTION

The invention relates to an optical force sensing element for microsurgical instruments, for measuring force F in three orthogonal directions x, y, z, comprising a monolithic cylinder structure with a bottom surface expanding in a plane x-y, an axis in direction z, a cylindrical surface surrounding the axis z and a top surface opposite the bottom surface suitable to absorb and transmit the force F to be measured.

BACKGROUND

In the field of minimally invasive microsurgery and therapy, in-vivo feedback information about the contact force exerted at the tip of instruments or tools is an important parameter required by surgeons to improve the outcome of their interventions. Frequently, the reduced access conditions affect the feel of interaction forces between the instruments and the tissues or organs being treated, and the forces involved are below the human perceptual thresholds.

A particular case of application of this invention relates to palpation procedures during middle-ear surgery, to evaluate the mobility of the ossicular chain during tympanoplasty. The knowledge about the ossicular mobility is important for decisions regarding surgical procedures as well as for the prognosis of improvement of hearing level. For example, typical contact forces on microsurgical tools for the evaluation of the mobility of the stapes bone are less that 10 mN, below the threshold of the operator's tactile sensitivity.

No such 3-dimensional force sensing tool for middle-ear is known. The only instrument reported is a tool for the evaluation of the stapes bone which measures only in one axial direction, as described in "An apparatus for diagnostics of ossicular chain mobility in humans" by Takuji Koike et al, International Journal of Audiology 2006; 45:121-128.

Another particular case of application of the invention relates to micro-force sensing tools for retinal microsurgery. Retinal microsurgery requires delicate manipulation of retinal tissues, and tool-to-tissue contact forces are frequently below human perceptual thresholds. Typical contact forces on microsurgical instrument tips during retinal surgery are less that 7.5 mN.

No such 3-dimensional force sensing tool for retinal surgery is known. An instrument is reported in which micro-forces in two lateral directions are measured using fibre Bragg grating techniques in "A sub-millimetri, 0.25 mN resolution fully integrated fibre-optic force sensing tool for retinal microsurgery" by Iulian Iordachita et al, published online 15 Apr. 2009 by International Journal of Computer Assisted Radiology and Surgery (Int J CARS).

It therefore would be desirable to provide a method for detecting and monitoring three-dimensional contact forces between the tip of a microsurgical instrument or tool and the tissue or organs to be explored and treated.

Known systems for catheter applications are reported to measure the contact forces at the tip of the catheter using fibre optical measuring techniques, where the force sensing elements are located close to the tip.

Force sensing elements for such microsurgical instruments used for catheter applications comprising monolithic cylinder structures are well known. By applying a three dimensional force on the tip of the structure, the structure is deformed in a predefined way given by a set of notches in the structure. These notches define several elastic zones making the structure flexible in some of the directions x, y and/or z. Optical fibres integrated in the structure admit to determine a displacement of individual parts of the structure, which is proportional to the force applied to the tip. The fibres enter the structure from the bottom of the structure and are guided in channels ending at one of the notches of the structure. Light emitted from the fibre is retro-reflected by a surface on the structure opposite of the fibre end. It re-enters the optical fibre and is evaluated to determine the distance of the fibre end to the surface on which the light was reflected.

Previously-know systems to measure contact forces at the tip of a catheter are described in US 20080009750. It relates to a monolithic structure which is very complicated in design and requires a rotation of the structure during manufacturing. Further, the structure is a tube with a wall thickness of 0.5 mm and a total diameter of 5 mm. It is not possible to reduce the size of such a structure for reasons of manufacturing and mechanical stability.

In US20090177095 a similar tube structure with three identical notches is shown, spaced apart from each other along the central axis. Each notch is made by a cut from one side which is in 120° rotation from the other two sides. In each of the three notches one optical fibre ends to measure the distance to the structure opposite the fibre end. It is inevitable that some of the fibres cross other notches until they reach their destination. The fixation of the fibres is very demanding. Although this structure must not be rotated during manufacturing of each single notch as the one mentioned before, it still must be rotated in-between cutting the notches. It is still very expensive for manufacturing in the required precision. Further, the structure is stiff in the axial direction and flexible in the radial directions, so it is suited only to detect forces applied on a tip close to the structure.

A further structure is given in WO2009114955. This structure is made by cutting in a plane defining blades in any of the planes x-y, x-z or y-z, defining the required flexible zones. Again, three optical fibres determine the distances of the gaps at the notches to determine the forces applied. This structure can be made smaller having a diameter less than 2.5 mm, between 1.7 and 2 mm. Unfortunately, the structure is very large in z-direction and complicated, containing 7 notches. Further versions shown in the same application are smaller in length and comprise only two or four cuts, but they are designed to be very flexible in the direction perpendicular to the axis.

These structures are simple for manufacturing but can not be used for the purpose indicated above, namely for middle-ear surgery or retinal microsurgery. Such tools contain a long and thin shaft at the front of the sensing structure with a tip, whereas a force applied at the distant tip in a direction perpendicular to the z-axis (in direction x, y) has an effect to the structure which is 5 to 20 times stronger than a force applied in the same direction but close to the structure due to the moment of inertia.

Further, it is more and more common that medical instruments become disposable for reducing the risk of infections. Therefore, the structure must be as simple as possible to be manufactured at low cost.

All structures known are used with catheters and therefore designed for lateral forces Fx, Fy and an axial force Fz, whereas the lateral forces are applied on the top of the structure close to the flexible area, not more distant to its flexible area than three times the diameter d of the structure.

These structures can not be used in surgery, where lateral forces are applied distant to the flexible zone of the structure, where the distance D is up to 20 times the diameter d of the structure. It has been shown that the known structures can not be adapted for this application by re-dimensioning of the structure.

BRIEF SUMMARY OF THE INVENTION

The problem to be solved is to describe an optical force sensing element for microsurgical instruments as described in the technical field of the invention, being manufactured at low cost and having a sensitivity which is 5 to 20 times higher in the z-direction axis of the structure than in the direction x-y perpendicular to the axis. A further problem is to describe a microsurgical instrument for middle-ear surgery or retinal microsurgery and a method for manufacturing a said element. Accuracy of the sensing element must be high and manufacturing costs low. Further, the element must have a small diameter d.

Each problem is solved by the features related to the said problems as described below.

The basic idea of the present invention is that the monolithic structure contains three notches, all of them made punch like from the same direction by forming two blades between them, and that the structure contains three optical fibres fixed inside channels parallel to the z-axis, entering the bottom surface and reaching to or near to the top surface, whereas the channels with their optical fibres cross only the first notch while bypassing the other two notches in the structure, and all fibres having a Fabry-Perot interferometric cavity within the first notch.

The three notches are preferably made by Wire-EDM (Electrical Discharge Machining). Since the notches in the structure are designed to be punch like, the structure must not be turned during the whole process of machining the notches. This increases the precision of the structure and lowers the costs of manufacturing.

An optical force sensing element for microsurgical instruments (22) measures force F in three orthogonal directions x, y, z, and includes a monolithic cylinder structure (1), a cylindrical surface (4) and a top surface (5) suitable to absorb and transmit the force F to be measured. The structure features three punch-like notches (6), all being parallel to the y-direction, spaced apart along the z-axis and forming exactly two blades (7) between the first notch (6) and the second notch (6) as well as between the second notch (6) and the third notch (6). The structure further comprises three channels (8) parallel to the z-axis, extending from the bottom surface (3) to the top surface (5) and crossing the first notch (6) while bypassing the other two notches (6) in the structure (2). The force sensing element further comprises three optical fibres (9), each fixed in one of the three channels (8), all entering the structure (2) from the bottom surface (3), crossing the first notch and ending at or near the top surface (5) while being interrupted in the first notch (6) so as to define two surfaces (10, 12) of each fibre that form Fabry-Perot interferometric cavities (13). The invention further relates to a microsurgical instrument comprising such an element and to a method for manufacturing such an element.

BRIEF DESCRIPTION OF THE DRAWINGS

The following figures illustrate preferred embodiments of the invention.

FIG. 5 shows a sectional view of the optical force sensing element of FIG. 4;

FIG. 6 a-c shows the channels with the optical fibres in three preferred versions.

DESCRIPTION OF EXEMPLARY EMBODIMENTS OF THE INVENTION

Figure 1:
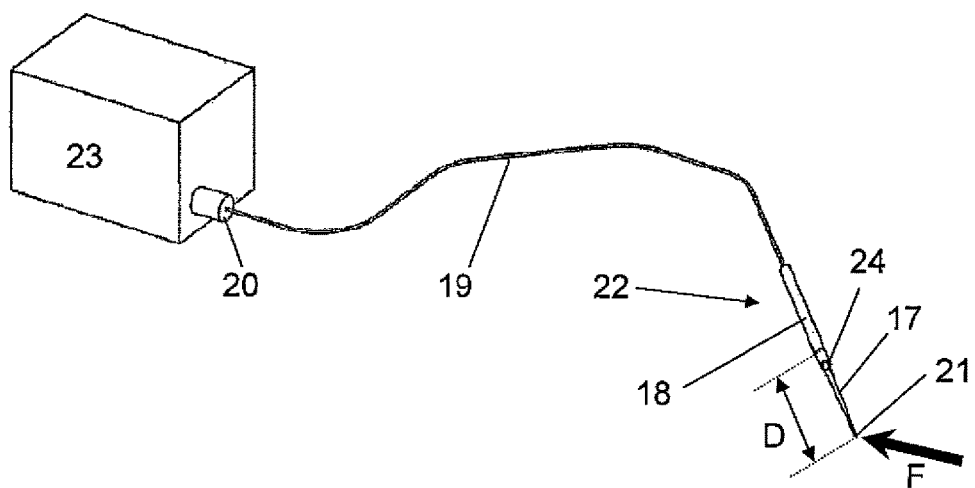
FIG. 1 is a schematic view of a microsurgical instrument according to the present invention connected to an evaluation unit.
Figure 2:
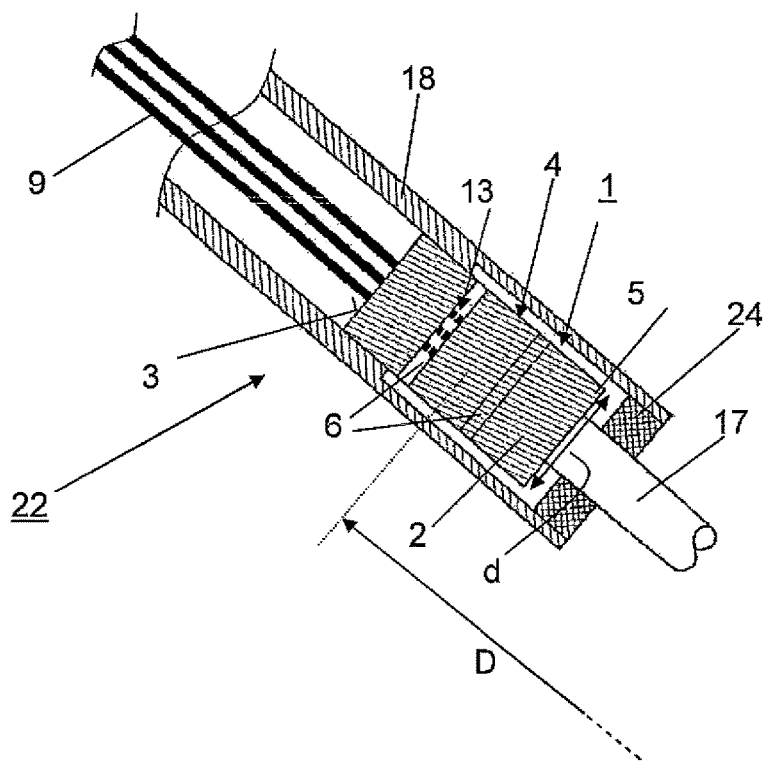
FIG. 2 shows a longitudinal cut through a microsurgical instrument according to the present invention.

The invention is described referring to the figures. FIG. 1 shows a schematic view of a microsurgical instrument 22 according to the present invention connected through optical fibres 9 in a cable 19 with a connector 20 to an evaluation unit 23, which is for example an opto-electronics unit composed of WLI signal conditioners for the reading of a gap lengths of Fabry-Perot-cavities and a microprocessor or computer for the computation of the force vector. The microsurgical instrument 22 can be hand-held by the surgeon or controlled by an automatic robotic system on its housing 18 containing an optical force sensing element 1 (FIG. 2). It further comprises a long and thin shaft 17 with a tip 21 which is attached to the optical force sensing element 1 (FIG. 2) in the housing 18. The total distance between the centre of the sensing element 1 and the tip 21 of the shaft 17 is the length D (FIG. 2). During use a three dimensional force $F_{xyz}$ is applied at the tip 21 and registered at the optical force sensing element 1. The measured information is transferred through the optical fibres 9 in the cable 19 and via the connector 20 to the evaluation unit 23.

As described in FIG. 2, the force sensor element 1 is located in the housing 18 behind the elongate shaft 17 which reaches out of the housing 18. The force sensor element 1 comprises a joint 16 where the shaft 17 is mounted firmly. The bottom surface 3 of the sensor element 1 is fixed firmly to the housing 18 whereas the rest of the sensor element 1 and the shaft 17 remain free and deform in response to the magnitude and direction of the force F applied at the tip 21. The sensor element is used to measure the 3-dimensional contact force F at the tip 21 of the shaft, whereas this tip 21 can be formed straight, in a 45°-angle hook-shape or in any other form suitable for surgery. The sensor element 1 is mounted inside the housing 18 so that it is well protected against lateral forces exerted by the fingers of the surgeon for example and to render the sensor element more easily hermetic to fluids or any external debris.

A flexible junction 24 is mounted between the housing 18 and the shaft 17 to seal hermetically the sensor element 1 and the optical fibres 9 fixed to it. The junction 24 can be a rubber gasket (o-ring) or a bellow shaped element, made of metallic or synthetic rubber material. The forces exerted by the flexible junction 24 to the shaft 17 must be small compared to the tip contact forces F.

On the other end of the housing, opposite the junction 24, the optical fibres 9 leave the housing inside the cable 19.

Figure 3:
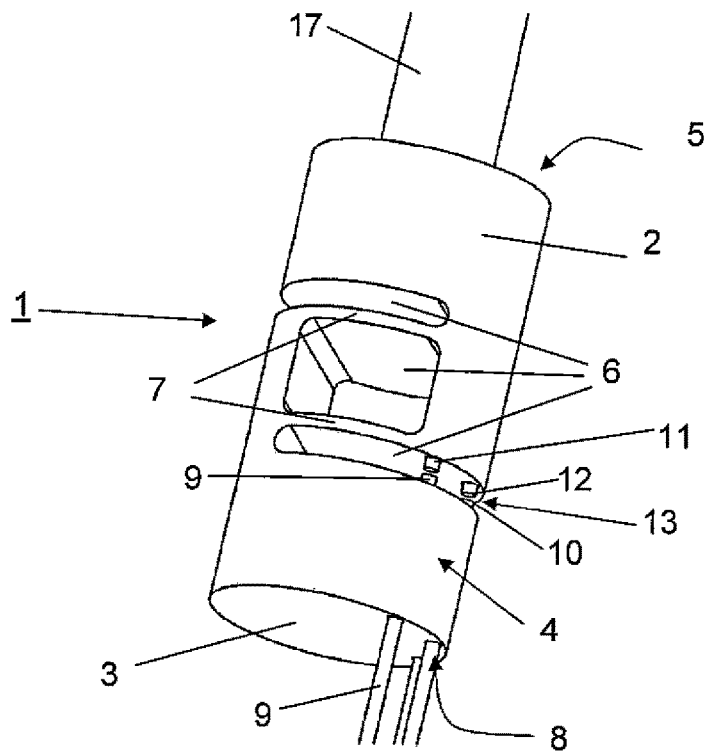
FIG. 3 shows a perspective view of an optical force sensing element according to the present invention.
Figure 4:
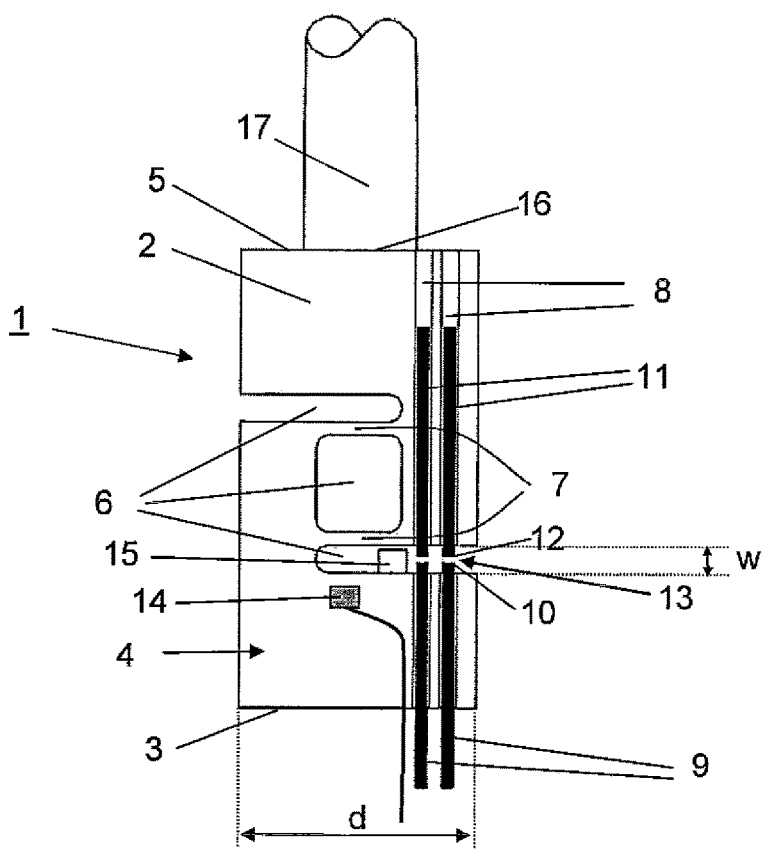
FIG. 4 shows a longitudinal cut through an optical force sensing element according to the present invention in a preferred embodiment.

In FIG. 3 and FIG. 4, an optical force sensing element 1 according to the present invention is shown in different views. The force sensor element 1 comprises a monolithic cylinder structure 2 with a bottom surface 3 expanding in a plane x-y, an axis in direction z, a cylindrical surface 4 surrounding the axis z and a top surface 5 opposite the bottom surface 3 suitable to absorb and transmit the force F to be measured. The top surface 5 preferably contains a joint 16 for mounting the shaft 17. Typically, the structure 2 has an outer diameter d in x-y direction of 0.5 to 4 mm, and can be machined with or without a through hole.

The structure features three punch-like notches 6, all being parallel to the y-direction. They are spaced apart along the z-axis and forming exactly two blades 7 in parallel x-y planes. The first blade 7 is between the first and the second notch 6, the second blade 7 is between the second and the third notch 6. All notches 6 are punch-like and parallel, so that they appear being made by punches expanding in x-z planes advancing through the structure 2 in the y direction. Typically, the blades 7 have a thickness in the z-direction of 0.02 to 0.4 mm.

In a preferred embodiment, the notches 6 are mirror-symmetric in respect to a middle x-z plane and the notches have 180° rotational symmetry according to a central y-axis.

The first and the third notch 6 are long openings formed in direction x and −x, parallel to each other, with preferably identical lengths in directions x, −x, overlapping each other, and with identical widths w in z-direction of 0.05 to 0.5 mm. The second notch 6 is a through hole in the centre of the structure 2. In direction x it preferably extends over the overlapping area of the first and second notch, whereas on direction z it extends over almost the entire area between the first and the third notch 6 leaving only two thin blades 7. Preferably, the overlapping area and therefore the width of the second notch 6 in direction x is at least one third of the diameter d of the structure 2. The remaining structures in direction x in the prolongations of the first and thirst notch 6 are relatively thin and permit a bending in the x and y direction, when a lateral force is applied at the tip 21 of the shaft. The two parallel thin blades 7 make the structure 2 flexible in direction z and stiff in the directions x and y. Considering that the influence of a force $F_{yx}$ at the tip 21 in direction x and y is amplified due to the leverage force to the structure and a force $F_z$ is not, the effects in the form of deformation on the structure in all three directions is comparable.

The structure 2 further comprises three channels 8 open or closed to the cylindrical surface 4 and parallel to the z-axis. They extend from the bottom surface 3 to or near to the top surface 5 and cross the first notch 6 only, while bypassing the other two notches 6 inside the structure 2. The force sensing element 1 further comprises three optical fibres 9 each fixed in one of the three channels 8. All of these fibres 9 are entering the structure 2 from the bottom surface 3, crossing the first notch 6 and ending at or near the top surface 5 while being interrupted in the first notch 6 defining sections of fibre 11. Where interrupted, the optical fibres 9 and sections of fibres 11 are forming two parallel surfaces 10, 12 by defining Fabry-Perot interferometric cavities 13. The two surfaces 10, 12 are obtained by cleaving, polishing or laser-cutting the fibre ends at 0°. The channels 8 serve to align precisely the fibres 9 with the sections of fibres 11 to form the cavities 13. The first notch 6 can be the one being the closest to the bottom surface 3 as shown in the figures, or it can be the one being the closest to the top surface 5 of the structure 2.

The fibres 9 and the sections of fibre 11 are fixed in the channels 8, preferably by adhesive, on both sides of the Fabry-Perot cavities.

Such a force sensor element 1 is suitable for microsurgical instruments 22, for measuring forces F having components in three orthogonal directions x, y, z, especially when the forces are applied distant to the sensing element.

Preferably the structure 2 is of titanium, ceramics, a polymer, stainless steel or non corrosive metal. Further, the thermal coefficient of expansion (TCE) of the structure 2 should be as close as possible to the TCE of the optical fibres 9 and/or of the sections of fibre 11 to reduce sensitivity to temperature changes. Since commercial optical fibres are made of fused silica material which has a very low TCE, to reduce temperature sensitivity, the sections of fibre 11 can be made of a different material with a TCE close to the TCE of the structure material. If desired, the structure 2 may also comprise a temperature sensing device 14 to monitor the temperature for possible needs for corrections.

To improve the light transfer, the two surfaces 10, 12 of each fibre at the Fabry-Perot interferometric cavity 13 can be coated with semi reflective coatings.

The lengths of the interferometric cavities 13 vary with the elastic deformation of the flexible structure due to forces exerted at the tip of the shaft. In neutral position the gap of each Fabry-Perot interferometric cavity 13 between the surface 10 of the optical fibre 9 and the surface 12 of the section of fibre 11 is typically between 0.01 to 0.1 mm.

The lengths of the cavities are measured using optical interferometry, in particular, the so called White Light Interferometry (WLI) using signal conditioners such as of the Company FISO in Canada. Finally, the forces are calculated based on a well known calibration procedure, where the magnitude and direction of the force vector is calculated from the three lengths of the optical cavities and a calibration matrix.

To prevent breaking the fibre-ends 10, 12 due to overloads resulting in mechanical contact of the two fibre-ends, the first notch 6 may comprise a mechanical stop 15.

When axial forces Fz are applied to the structure 2, the two blades 7 bend resulting in a parallel axial translation of the structure so that all three Fabry-Perot cavities experience the same change in length. On the other hand, when lateral forces Fxy are applied to the tip 21 of the shaft 17, because of the relatively long distance between the tip 21 and the structure 2, since the moment of inertia or torque is large, the whole structure tends to bend laterally both at the level of the two blades 7 as well as at the level of the two flexure portions resulting from the first and the third lateral notches 6. In this case, the 3 cavities experience differential changes depending on their location and on the direction of the applied lateral force.

The present structure 2 is suited for forces applied at long distances D from the centre of the sensing element 1. The ratio R=D/d, where D is the distance between the tip 21 and the centre of the sensing element 1 and d the diameter of the structure 2, is typically between 5 and 20.

The main advantages of this invention are that the element 1 according to the invention is easy to manufacture, that it allows small dimensions in length and in diameter d, that it can be manufactured with or without a through hole, that it can be mounted distant to the tip 21, and that it shows only very small effects to temperature dilatation because the fibres 9 and sections of fibre 11 are fixed to the structure 2 all along the grooves or holes except for the flexible zone with the first notch 6. The bottom surface 3 of the cylinder structure 2 as well as any of its cross section can have a circular, square or any other shape.

As described in FIG. 5, by cutting the structure in the x-y plane in the centre, the three channels 8 with the fibres can be seen within the structure 2 next to the second notch 6. The effective change in the individual gap length due to the applied force can be optimized by selecting the position of the each channel 8 within the structure 2.

As described in FIGS. 6 *a, b* and *c*, the fibres 9 can be fixed in different kind of channels 8. In FIG. 6*a* the channels are closed being closed through holes parallel to the cylindrical surface 4 of the structure 2, whereas at FIG. 6*b* and FIG. 6*c* the channels 8 are open to the cylindrical surface 4. The fibres may be placed in lateral-gap through holes shown in FIG. 6*b* or in open lateral grooves as shown in 6*c*. The advantage of the open lateral grooves is the easy inserting of the fibres in the channel 8 during assembly and the easy manufacturing process.

The fibres 9 and the sections of fibre 11 are fixed inside the channels 8 for example using epoxies or UV curable adhesives. They may also be brazed or mechanically clamped in position.

The optical force sensing element 1 can be manufactured small enough to fit inside a handle of a typical microsurgical instrument 22 and measure with precision the contact forces F applied at the distal tip 21 of the elongate shaft 17, with a typical outer diameter d between 1 and 4 mm.

Typical shaft 17 length of a surgical instrument 22 is about 40 mm, which corresponds to the effective distance between the sensing element 1 and the tip 21 of the shaft 17 where the contact forces F are applied.

For hand held instruments 22, the handle is typically 10 cm to 15 cm long and 5 mm in diameter d. These dimensions allow the operators to handhold comfortably and with precision the tool and have as well a good visibility of the tool shaft and tip when working with microscopes in small orifices with difficult access, as in the case of middle-ear surgery or retinal microsurgery.

The main advantage of the inventive structure 2 is that it is machined in only one direction, which makes it easy and cheap to manufacture. There is no need of a tubular structure. The fibres can be fixed not only on or near the surface of the structure 2 but also inside the structure 2 profile.

The flexible structures 2 are preferably manufactured by turning (décolletage) or by electro-discharge machining (EDM), or by a combination of both. They may also be machined by laser cutting or sawing, or a combination. The structures can be a metallic material, a ceramic or a polymer. Preferably titanium or stainless steel is selected.

To produce an optical force sensing element 1, three optical fibres 9 with cleaved or polished fibre-ends 10 at 0° are entered into the open or closed channels 8 of the structure 2 from the bottom surface 3, reaching the first notch 6, and three sections of fibres 11 with cleaved or polished fibre-ends 12 at 0° are entered into the channels 8 from the top surface 5 reaching the first notch 6. The six fibres 9, 11 are fixed to the structure 2 on both sides of the first notch 6, defining the Fabry-Perot interferometric cavities 13 with the fibre-end surfaces 10, 12 parallel to each other.

In another embodiment, to produce an optical force sensing element 1, three single continuous optical fibres 9 are entered into the open or closed channels 8 of the structure 2 with the notches 6 from the bottom surface 3, passing the first notch 6 and reaching to or near to the top surface 5. The three continuous optical fibres 9 are fixed to the structure 2 on both sides of the first notch 6. Then, the optical fibres 9 are laser-cut in the area of the first notch 6 defining the Fabry-Perot interferometric cavities 13 and separating the continuous optical fibres 9 into the optical fibres 9 and sections of fibre 11.

Typically, when using white light interferometry, with for example FISO signal conditioners, to read the cavity lengths 13 of the Fabry-Perot interferometers, the flexible structures 2 are designed so that the magnitude of the deformation of the cavity 13 is of the order of 1 micron to 10 microns for the maximum applied force F in any direction at the tip. The maximum applied force F depends on the desired application of the tool, which may be of the order of 1N for middle-ear surgery palpation procedures and of the order of 0.1N for retinal surgery.

REFERENCES

1 optical force sensing element
2 structure, monolithic, cylindrical
3 bottom surface
4 cylindrical surface
5 top surface
6 notches
7 blades
8 channels
9 optical fibres
10 surface of optical fibres
22 sections of fibre
12 surface of sections of optical fibre
13 Fabry-Perot interferometric cavities, distance, gap
14 temperature sensing device
15 mechanical stop
16 joint
17 shaft
18 housing
19 cable
20 connector
21 tip of the shaft
22 microsurgical instrument
23 evaluation unit
24 flexible junction
F force
w width of first notch
D distance from the centre of the structure to the tip of the shaft
d outer diameter

The invention claimed is:

1. Optical force sensing element for microsurgical instruments, for measuring force (F) in three orthogonal directions x, y, z, comprising:
   a monolithic cylinder structure with a planar bottom surface disposed in an x-y plane, the monolithic cylinder structure having an axis of rotation disposed normal to the x-y plane and parallel to the z direction, the monolithic cylinder structure defining a cylindrical surface disposed radially equidistant from the axis of rotation, the cylindrical surface defining opposite ends, and the monolithic cylinder structure having at one end of the cylindrical surface a top surface, the monolithic cylinder structure having the planar bottom surface at the end opposite to the top surface of the cylindrical surface, the length of the monolithic cylinder structure extending in the z direction from the top surface to the planar bottom surface, the top surface being configured to receive and transmit the force (F) to be measured,
   the cylindrical surface of the monolithic cylinder structure being interrupted by three notches, a first notch disposed closer to the planar bottom surface than the other two notches, a third notch disposed closer to the top surface than the other two notches and a second notch disposed between the first notch and the third notch, a first blade disposed between the first notch and the second notch and a second blade disposed between the second notch and the third notch, the monolithic cylinder structure further comprises three channels extending parallel to the z-axis, each channel extending from and through the planar bottom surface to the top surface and intersecting the first notch while not intersecting the other two notches in the monolithic cylinder structure, three optical fibres, each optical fibre fixed in one of the three channels, each optical fibre extending out of the monolithic cylinder structure from the planar bottom surface, each optical fibre ending at or near the top surface, each optical fibre having a first portion extending in the z direction through the first notch, the first portion of each optical fibre defining a cut along the x-y direction that severs the first portion into two sections to form two opposing optical fibre surfaces that are disposed within the first notch at the cut and define a Fabry-Perot interferometric cavity, the first section of the two sections is a lower section of each optical fibre extending from within the first notch and through the planar bottom surface of the monolithic cylinder structure, the second section of the two sections is an upper section of each optical fibre extending from within the first notch to at or near the top surface of the monolithic cylinder structure.

2. An optical force sensing element according to claim 1, whereas each of the channels extends through the cylindrical surface all along the length of the monolithic cylinder structure.

3. An optical force sensing element according to claim 1, whereas the optical fibres are fixed in the channels by adhesive.

4. An optical force sensing element according to claim 1, whereas the monolithic cylinder structure is formed of at least one of the following materials: titanium, ceramics, a polymer, stainless steel or non corrosive metal.

5. An optical force sensing element according to claim 1, whereas a middle x-z plane includes the axis of rotation and is perpendicular both the top surface and the planar bottom surface and each of the notches is mirror-symmetric with respect to the middle x-z plane.

6. An optical force sensing element according to claim 1, whereas the monolithic cylinder structure contains a temperature sensing device.

7. An optical force sensing element according to claim 1, whereas in neutral position the cut of each Fabry-Perot interferometric cavity measured along the z direction between the two surfaces of each interrupted optical fibre is between 0.01 to 0.1 mm.

8. An optical force sensing element according to claim 1, whereas the first notch has a width (w) in the z-direction of 0.05 to 0.5 mm.

9. An optical force sensing element according to claim 1, whereas the first notch comprises a mechanical stop to protect the two surfaces of each fibre that define the Fabry-Perot interferometric cavity.

10. An optical force sensing element according to claim 1, whereas the monolithic cylinder structure has an outer diameter (d) in the x-y direction of 0.5 to 4 mm.

11. An optical force sensing element according to claim 1, whereas the monolithic cylinder structure has blade thickness of 0.02 to 0.4 mm in the z direction.

12. An optical force sensing element according to claim 1, whereas the two surfaces of each interrupted fibre that define each Fabry-Perot interferometric cavity are coated with semi-reflective coatings.

13. An optical force sensing element according to claim 1, whereas the thermal coefficient of expansion (TOE) of the monolithic cylinder structure matches the TOE of the lower sections of each of the interrupted optical fibres.

14. An optical force sensing element according to claim 1, whereas the thermal coefficient of expansion (TCE) of the upper sections of each of the interrupted optical fibres matches the TCE of the monolithic cylinder structure.

15. An optical force sensing element according to claim 1, whereas the top surface contains a joint for mounting a shaft.

16. An optical force sensing element according to claim 1, wherein the majority of the second notch has a uniform dimension measured in the z direction and the second notch extends continuously through diametrically opposite regions of the cylindrical surface and the second notch extends through the monolithic cylinder structure disposed between these opposite diametrically opposite regions of the cylindrical surface.

17. A microsurgical instrument containing comprising:
optical force sensing element for microsurgical instruments, for measuring force (F) in three orthogonal directions x, y, z, comprising:
a monolithic cylinder structure with a planar bottom surface disposed in an x-y plane, the monolithic cylinder structure having an axis of rotation disposed normal to the x-y plane and parallel to the z direction, the monolithic cylinder structure defining a cylindrical surface disposed radially equidistant from the axis of rotation, the cylindrical surface defining opposite ends, and the monolithic cylinder structure having at one end of the cylindrical surface a top surface, the monolithic cylinder structure having the planar bottom surface at the end opposite to the top surface of the cylindrical surface, the length of the monolithic cylinder structure extending in the z direction from the top surface to the planar bottom surface, the top surface being configured to receive and transmit the force (F) to be measured,
the cylindrical surface of the monolithic cylinder structure being interrupted by three notches, a first notch disposed closer to the planar bottom surface than the other two notches, a third notch disposed closer to the top surface than the other two notches and a second notch disposed between the first notch and the third notch,
a first blade disposed between the first notch and the second notch and a second blade disposed between the second notch and the third notch,
the monolithic cylinder structure further comprises three channels extending parallel to the z-axis, each channel extending from and through the planar bottom surface to the top surface and intersecting the first notch while not intersecting the other two notches in the monolithic cylinder structure,
three optical fibres, each optical fibre fixed in one of the three channels, each optical fibre extending out of the monolithic cylinder structure from the planar bottom surface, each optical fibre ending at or near the top surface, each optical fibre having a first portion extending in the z direction through the first notch, the first portion of each optical fibre defining a cut along the x-y direction that severs the first portion into two sections to form two opposing optical fibre surfaces that are disposed within the first notch at the cut and define a Fabry-Perot interferometric cavity, the first section of the two sections is a lower section of each optical fibre extending from within the first notch and through the planar bottom surface of the monolithic cylinder structure, the second section of the two sections is an upper section of each optical fibre extending from within the first notch to at or near the top surface of the monolithic cylinder structure;

a housing, wherein the optical force sensing element is mounted in the housing;

a cable, wherein the optical fibres are contained in the cable with a connector; and a long shaft mounted on the top surface of the monolithic cylinder structure, wherein the long shaft extends outside the housing and the long shaft has a defined tip at a distal end.

* * * * *